(12) United States Patent
Chen

(10) Patent No.: US 7,022,372 B1
(45) Date of Patent: Apr. 4, 2006

(54) COMPOSITIONS FOR COATING IMPLANTABLE MEDICAL DEVICES

(75) Inventor: Yung-Ming Chen, Cupertino, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 177 days.

(21) Appl. No.: 10/293,177

(22) Filed: Nov. 12, 2002

(51) Int. Cl.
A61L 17/00 (2006.01)

(52) U.S. Cl. .................................................. 427/2.25

(58) Field of Classification Search ................ 424/423
See application file for complete search history.

(56) References Cited

U.S. PATENT DOCUMENTS

| | | | |
|---|---|---|---|
| 2,072,303 A | 3/1937 | Herrmann et al. ........ 128/335.5 |
| 4,269,713 A | 5/1981 | Yamashita et al. |
| 4,329,383 A | 5/1982 | Joh |
| 4,733,665 A | 3/1988 | Palmaz ........................ 128/343 |
| 4,800,882 A | 1/1989 | Gianturco .................... 128/343 |
| 4,839,055 A | 6/1989 | Ishizaki et al. |
| 4,886,062 A | 12/1989 | Wiktor ........................ 128/343 |
| 4,941,870 A | 7/1990 | Okada et al. |
| 4,977,901 A | 12/1990 | Ofstead ....................... 128/772 |
| 4,985,285 A | 1/1991 | Ichikawa et al. |
| 5,112,457 A | 5/1992 | Marchant .................... 204/165 |
| 5,165,919 A | 11/1992 | Sasaki et al. |
| 5,328,471 A | 7/1994 | Slepian ........................ 604/101 |
| 5,417,981 A | 5/1995 | Endo et al. |
| 5,455,040 A | 10/1995 | Marchant |
| 5,464,650 A | 11/1995 | Berg et al. ..................... 427/2.3 |
| 5,578,073 A | 11/1996 | Haimovich et al. ............ 623/1 |
| 5,605,696 A | 2/1997 | Eury et al. .................... 424/423 |
| 5,628,730 A | 5/1997 | Shapland et al. .............. 604/21 |
| 5,667,767 A | 9/1997 | Greff et al. ............... 424/9.411 |
| 5,670,558 A | 9/1997 | Onishi et al. ................. 523/112 |
| 5,700,286 A | 12/1997 | Tartaglia et al. ............... 623/1 |
| 5,713,119 A | 2/1998 | Lagatta |
| 5,716,981 A | 2/1998 | Hunter et al. ................ 514/449 |
| 5,756,553 A | 5/1998 | Iguchi et al. |
| 5,770,301 A | 6/1998 | Murai et al. |
| 5,800,392 A | 9/1998 | Racchini ....................... 604/96 |
| 5,824,049 A | 10/1998 | Ragheb et al. ................. 623/1 |
| 5,830,178 A | 11/1998 | Jones et al. .................... 604/49 |
| 5,837,313 A | 11/1998 | Ding et al. ................. 427/2.21 |
| 5,851,508 A | 12/1998 | Greff et al. ............... 424/9.411 |
| 5,858,746 A | 1/1999 | Hubbell et al. .............. 435/177 |
| 5,865,814 A | 2/1999 | Tuch ............................ 604/265 |
| 5,871,437 A | 2/1999 | Alt |
| 5,873,904 A | 2/1999 | Ragheb et al. ................. 623/1 |
| 5,897,955 A | 4/1999 | Drumheller |
| 5,957,879 A | 9/1999 | Roberts et al. |
| 5,971,954 A | 10/1999 | Conway et al. ............... 604/96 |
| 5,980,928 A | 11/1999 | Terry ............................ 424/427 |
| 5,980,972 A | 11/1999 | Ding ............................ 427/2.24 |
| 5,997,517 A | 12/1999 | Whitbourne ................. 604/265 |
| 6,010,530 A | 1/2000 | Goicoechea .................... 623/1 |
| 6,015,541 A | 1/2000 | Greff et al. ................ 424/1.25 |
| 6,031,028 A | 2/2000 | Iino et al. |
| 6,040,415 A | 3/2000 | Arimori et al. |
| 6,042,875 A | 3/2000 | Ding et al. |
| 6,051,648 A | 4/2000 | Rhee et al. .................. 525/54.1 |
| 6,056,993 A | 5/2000 | Leidner et al. .............. 427/2.25 |
| 6,060,451 A | 5/2000 | DiMaio et al. ................ 514/13 |
| 6,080,488 A | 6/2000 | Hostettler et al. ........ 428/426.3 |
| 6,096,070 A | 8/2000 | Ragheb et al. .................. 623/1 |
| 6,099,562 A | 8/2000 | Ding et al. .................. 623/1.46 |
| 6,110,188 A | 8/2000 | Narciso, Jr. .................. 606/153 |
| 6,110,483 A | 8/2000 | Whitbourne et al. |
| 6,113,629 A | 9/2000 | Ken ............................. 623/1.1 |
| 6,120,536 A | 9/2000 | Ding et al. .................. 623/1.43 |
| 6,120,904 A | 9/2000 | Hostettler et al. ........ 428/423.3 |
| 6,121,027 A | 9/2000 | Clapper et al. .............. 435/180 |
| 6,129,761 A | 10/2000 | Hubbell ......................... 623/11 |
| 6,153,252 A | 11/2000 | Hossainy et al. ............. 427/2.3 |
| 6,165,212 A | 12/2000 | Dereume et al. ........... 623/1.13 |
| 6,245,753 B1 | 6/2001 | Byun et al. |
| 6,258,121 B1 | 7/2001 | Yang et al. ................. 623/1.46 |
| 6,259,054 B1 | 7/2001 | Broadhead |
| 6,287,628 B1 | 9/2001 | Hossainy et al. ............. 427/2.3 |
| 6,331,313 B1 | 12/2001 | Wong et al. |
| 6,335,029 B1 | 1/2002 | Kamath et al. |
| 6,368,658 B1 | 4/2002 | Schwarz et al. |
| 6,379,381 B1 | 4/2002 | Hossainy et al. ........... 623/1.42 |
| 6,451,373 B1* | 9/2002 | Hossainy et al. ........... 427/2.25 |
| 6,503,954 B1 | 1/2003 | Bhat et al. |
| 6,555,157 B1 | 4/2003 | Hossainy |
| 6,620,194 B1 | 9/2003 | Ding et al. |
| 2001/0037145 A1 | 11/2001 | Guruwaiya et al. |

FOREIGN PATENT DOCUMENTS

| | | |
|---|---|---|
| EP | 0 310 856 | 2/1989 |
| EP | 0 665 023 | 8/1995 |
| EP | 0 879 595 | 11/1998 |
| EP | 0 970 711 | 1/2000 |
| WO | WO 91/12846 | 9/1991 |
| WO | WO 96/40174 | 12/1996 |
| WO | WO 97/45105 | 12/1997 |
| WO | WO 98/17331 | 4/1998 |
| WO | WO 99/01118 | 1/1999 |
| WO | WO 99/63981 | 12/1999 |
| WO | WO 00/02599 | 1/2000 |
| WO | WO 00/12147 | 3/2000 |
| WO | WO 00/64506 | 11/2000 |
| WO | WO 01/01890 | 1/2001 |
| WO | WO 01/45763 | 6/2001 |

OTHER PUBLICATIONS

Anonymous, *Rolling Therapeutic Agent Loading Device for Therapeutic Agent Delivery or Coated Stent* (Abstract 434009), Res. Disclos. p. 975 (Jun. 2000).

(Continued)

*Primary Examiner*—Carlos A. Azpuru
*Assistant Examiner*—Casey Hagopian
(74) *Attorney, Agent, or Firm*—Squire, Sanders & Dempsey L.L.P.

(57) ABSTRACT

A method for coating an implantable medical device, comprising dissolving a polymer in a solvent mixture which includes co-solvents having low viscosity, low surface energy or low dielectric constant.

18 Claims, No Drawings

OTHER PUBLICATIONS

Barath et al; *Low Dose of Antitumor Agents Prevents Smooth Muscle Cell Proliferation After Endothelial Injury* JCAA 13(2):252A (1989).

Dichek et al., *Seeding of Intravascular Stents with Genetically Engineered Endothelial Cells,* Circ. 80(5):1347-1353 (1989).

Herdeg et al., *Antiproliferative Stent Coatings: Taxol and Related Compounds,* Semin. Intervent. Cardiol. 3:197-199 (1998).

Matsumaru et al.; *Embolic Materials for Endovascular Treatment of Cerebral Lesions,* J. Biomater. Sci. Polymer Edn. 8(7):555-569 (1997).

Miyazaki et al.; *Antitumor effect of Implanted Ethylene-Vinyl Alcohol Copolymer Matrices Containing Anticancer Agents on Ehrlich Ascites Carcinoma and P388 Leukemia in Mice;* Chem. Pharm. Bull. 33(6):2490-2498 (1985).

Miyazawa et al.; *Effects of Pemirolast and Tranilast on Intimal Thickening After Arterial Injury in the Rat,* J. Cardiovasc. Pharmacol., pp. 157-162 (1997).

Ohsawa et al.; *Preventive Effects of an Antiallergic Drug, Pemirolast Potassium, on Restenosis After Percutaneous Transluminal Coronary Angioplasty:* American Heart Journal; pp. 1081-1087 (1998).

Shigeno; *Prevention of Cerebrovascular Spasm By Bosentan, Novel Endothelin Receptor,* Chemical Abstract 125:212307 (1996).

Forrester et al., *A Paradigm for Restenosis Based on Cell Biology: Clues for the Development of New Preventive Therapies,* J. Am. Coll. Cardio 17, (1991), pp. 758-769.

* cited by examiner

COMPOSITIONS FOR COATING IMPLANTABLE MEDICAL DEVICES

BACKGROUND OF THE INVENTION

1. Field of the Invention

This invention relates to compositions for coating drug delivery devices, such as drug eluting vascular stents.

2. Description of the State of the Art

In the field of medical technology, there is frequently a necessity to administer drugs locally. To provide an efficacious concentration to the treatment site, systemic administration of such medication can produce adverse or toxic side effect for the patient. Local delivery is a preferred method in that smaller total levels of medication are administered in comparison to systemic dosages, but are concentrated at a specific site. Thus, local delivery produces fewer side effects and achieves more effective results.

One commonly applied technique for local delivery of a drug is through the use of medicated stents. One method of medicating a stent is with the use of a polymer coating incorporating an active agent. References describe a variety of polymers which can be used to coat stents. Of particular interest is poly(ethylene-co-vinyl alcohol) or EVOH, also known under the trade name EVAL manufactured by EVAL Company of America of Lisle, Ill. EVAL is also distributed commercially by Aldrich Chemical Company of Milwaukee, Wis.

EVAL is a product of hydrolysis of ethylene-vinyl acetate copolymers. Those having ordinary skill in the art of polymer chemistry will understand that EVAL may also be a terpolymer and may include up to 5% (molar) units derived from styrene, propylene and other suitable unsaturated monomers. The EVAL-based stent coating is usually fabricated by preparing a solution of EVAL in a suitable organic solvent or blend of solvents followed by applying the solution onto the stent, for example, by spraying or dipping.

Solvents currently used to prepare the EVAL coating formulation include dimethylacetamide (DMAC) and dimethylsulfoxide (DMSO). These solvents can dissolve EVAL and have been used very effectively to provide an excellent coating. However, their relatively high surface energy, viscosity and degree of wetting of the substrate can lead to a less than optimal coating quality. In addition, the weight of the coating formed per cycle of spraying can be improved resulting in a shorter duration of the coating process.

In view of the foregoing, improvements to the carrying the polymer can be made.

SUMMARY

According to one embodiment of this invention, a method for coating an implantable medical device is provided, the method comprises dissolving a poly(ethylene-co-vinyl alcohol) in a solvent system comprising a first solvent and a co-solvent to form a polymer solution, wherein the co-solvent is an organic solvent having the dielectric constant less than about 10 at room temperature, and applying the polymer solution onto the medical device to form the coating. The co-solvent comprises unsubstituted or substituted aliphatic hydrocarbons, unsubstituted or substituted cycloaliphatic hydrocarbons, or unsubstituted or substituted aromatic hydrocarbons, for example, n-pentane, n-hexane, n-heptane, cyclopentane, cyclohexane, benzene, toluene, carbon tetrachloride, methylene chloride, and tetrahydrofuran, and mixtures thereof.

According to another embodiment of this invention, a method for coating an implantable medical device is provided, the method comprises dissolving a poly(ethylene-co-vinyl alcohol) in a solvent system comprising a first solvent and a co-solvent to form a polymer solution, wherein the co-solvent is an organic solvent having surface energy less than about 30 dyne/cm at room temperature, and applying the polymer solution onto the medical device to form the coating.

According to yet another embodiment of this invention, a method for coating an implantable medical device is provided, the method comprises dissolving a poly(ethylene-co-vinyl alcohol) in a solvent system comprising a first solvent and a co-solvent to form a polymer solution, wherein the co-solvent is an organic solvent having a viscosity not exceeding about 1 centipoise at room temperature, and applying the polymer solution onto the medical device to form the coating.

DETAILED DESCRIPTION

A coating for an implantable medical device, such as a stent, according to one embodiment of the present invention, can include an optional primer layer, a drug-polymer layer (also referred to as a "reservoir layer"), and an optional topcoat layer. The primer layer can be applied between the stent and the drug-polymer layer to improve the adhesion of the drug-polymer layer to the stent. The drug-polymer layer can be applied onto the primed stent surface or directly onto the stent surface to serve as a reservoir for a therapeutic substance. The topcoat layer can reduce the rate of release of the drug from the reservoir layer.

One example of a polymer that can be used to fabricate the drug-polymer layer, the topcoat, and/or the primer layer is EVAL. Alternatively, other polymers can be used, for example, polyurethanes or polyacrylates.

According to one embodiment, a formulation for making the drug-polymer layer comprises a solution which includes EVAL and a therapeutic substance dissolved in a solvent system. The solution can be applied on the stent by a commonly known technique known to those having ordinary skill in the art, for example by spraying or dipping.

DMAC or DMSO can be used as the solvent to make the formulation for fabricating the drug-polymer layer. According to embodiments of the present invention, a solvent system can be used in which a fraction of DMAC or DMSO can be replaced in the formulation. The solvent system can comprise either DMAC or DMSO and a co-solvent. The co-solvent can have at least one of the following properties:

(a) viscosity at room temperature (~20° C.) not exceeding about 1 centipoise;
(b) surface energy at room temperature less than about 30 dyne/cm (0.03 N/m); and
(c) dielectric constant at room temperature less than about 10.

Suitable co-solvents include unsubstituted or substituted aliphatic, cycloaliphatic and aromatic hydrocarbons such as $C_5$–$C_7$ hydrocarbons, and mixtures thereof. The aliphatic hydrocarbons can be straight-chained or branched. Examples of co-solvents include n-pentane, n-hexane, n-heptane, cyclopentane, cyclohexane, benzene and toluene, and mixtures thereof. Examples of other suitable organic co-solvents include tetrahydrofuran, and halogenated low hydrocarbons such as carbon tetrachloride or methylene chloride. Examples of some suitable co-solvents and some of their properties are summarized in Table 1.

TABLE 1

Properties of Suitable Co-Solvents at Room Temperature

| No. | Co-Solvent | Viscosity, centipoise | Surface Energy, dyne/cm | Dielectric Constant, |
|---|---|---|---|---|
| 1 | n-Pentane | 0.23 | 15.5 | 1.84 |
| 2 | n-Hexane | 0.31 | 17.9 | 1.88 |
| 3 | n-Heptane | 0.42 | 20.3 | 1.92 |
| 4 | Cyclopentane | 0.44 | 22.4 | 1.97 |
| 5 | Cyclohexane | 1.00 | 24.9 | 2.02 |
| 6 | Benzene | 0.65 | 23.7 | 2.29 |
| 7 | Toluene | 0.59 | 28.5 | 2.38 |
| 8 | Tetrahydrofuran | 0.55 | 26.4 | 7.58 |
| 9 | Carbon tetrachloride | 0.97 | 26.7 | 2.29 |
| 10 | Methylene chloride | 0.18 | 26.5 | 9.08 |

The ratio between DMAC or DMSO and a co-solvent in the solvent system can be within a range of between about 3:1 and 9:1 (by mass), for example, about 4:1. In other words, a co-solvent can comprise between about 10 and 25 mass %, for example, about 20% of the total solvent system, and the balance is DMAC or DMSO.

To prepare the coating compositions, EVAL can be dissolved in the solvent system. The concentration of EVAL can be between about 1 and 5 mass %, for example, about 4 mass %. One factor that can be considered by those having ordinary skill in the art when choosing the concentration of the EVAL solution is the solution's viscosity. In one embodiment, the EVAL solution can have viscosity less than about 7.0 centipoise at room temperature so that the solution can be effectively atomized using a standard EFD nozzle, and sprayed onto the stent.

A therapeutic substance or drug can be added to the EVAL solution. The drug can include any substance capable of exerting a therapeutic or prophylactic effect for a patient. For example, the drug could be designed to inhibit the activity of vascular smooth muscle cells. It can be directed at inhibiting abnormal or inappropriate migration and/or proliferation of smooth muscle cells to inhibit restenosis. The drug may include small molecule drugs, peptides or proteins. Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co. of Stamford, Conn.), docetaxel (e.g. Taxotere®, from Aventis S.A. of Frankfurt, Germany) methotrexate, azathioprine, vincristine, vinblastine, fluorouracil, doxorubicin hydrochloride (e.g. Adriamycin® from Pharmacia & Upjohn of Peapack N.J.), and mitomycin (e.g. Mutamycin® from Bristol-Myers Squibb). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc. of Cambridge, Mass.). Examples of such cytostatic or antiproliferative agents include angiopeptin, angiotensin converting enzyme inhibitors such as captopril (e.g. Capoten® and Capozide® from Bristol-Myers Squibb), cilazapril or lisinopril (e.g. Prinivil® and Prinzide® from Merck & Co., Inc. of Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis of New York, N.Y.), 40-O-(3-hydroxy)propyl-rapamycin, 40-O-[2-(2-hydroxy)ethoxy]ethyl-rapamycin, and 40-O-tetrazole-rapamycin.

The coating of the present invention has been described in conjunction with a stent. However, the coating can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Some embodiments of the present invention are illustrated by the following Example. A first composition was prepared, the composition comprising:
  (a) about 4.0 mass % of EVAL; and
  (b) the balance, a solvent system comprising DMAC and n-pentane, with the mass ratio between DMAC and pentane of about 4:1.

To make the first composition, EVAL was combined with the DMAC/n-pentane system, and the mixture was stirred for about 2 hours at a temperature of about 80° C. The first composition was applied onto a stent to form a primer layer. To apply the primer layer, a spray apparatus, such as an EFD 780S spray nozzle with a VALVEMATE 7040 control system, manufactured by EFD, Inc. of East Providence, R.I. was used. The EFD 780S spray nozzle is an air-assisted external mixing atomizer. The first composition was atomized by air and applied to the stent surfaces. During the process of applying the composition, the stent can be optionally rotated about its longitudinal axis, at a speed of 50 to about 200 rpm. The stent can be also linearly moved along the same axis during the application.

The first composition was applied to a 18-mm PENTA stent (available from Guidant Corporation) in a series of 10-second passes, to deposit about 10 µg of coating per spray pass. Instead of the 18-mm PENTA stent, another suitable stent can be used, for example, a 18-mm VISION stent (also available from Guidant Corporation). Between the spray passes, the stent was dried for about 10 seconds using heated air with a temperature of about 80° C. Six to seven spray passes were applied, followed by baking the primer layer at about 140° C. for one hour. As a result, a primer layer was formed having a solids content of about 50 µg. "Solids" means the amount of the dry residue deposited on the stent after all volatile organic compounds (e.g., the solvent) have been removed.

A second composition was prepared comprising:
(c) about 4.0 mass % of EVAL;
(d) about 2.0 mass % of EVEROLIMUS; and
(e) the balance, a solvent system comprising DMAC and pentane, with the mass ratio between DMAC and pentane of about 4:1.

To make the second composition, EVAL was combined with the DMAC/n-pentane system, and the mixture was stirred for about 2 hours at a temperature of about 80° C., followed by adding EVEROLIMUS to the EVAL solution.

The second was sprayed to the primed stent to form a reservoir layer. In a manner identical to the application of the primer layer, forty spray passes were performed (depositing about 20 µg of coating per spray pass), followed by baking the reservoir layer at about 50° C. for about 2 hours, to form the reservoir layer having a solids content of about 30 µg.

A third composition was prepared, the composition comprising:
(f) about 4.0 mass % of EVAL; and
(g) the balance, a solvent system comprising DMAC and n-pentane, with the mass ratio between DMAC and pentane of about 4:1.

To make the third composition, EVAL was combined with the DMAC/n-pentane system, and the mixture was stirred for about 2 hours at a temperature of about 80° C. The third composition was applied onto a stent to form a topcoat layer. In a manner identical to the application of the primer layer, five spray passes were performed, followed by baking the reservoir layer at about 140° C. for about 1 hour, to form the topcoat layer having a solids content of about 50 µg.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for coating an implantable medical device, comprising:
(a) dissolving a poly(ethylene-co-vinyl alcohol) and a drug in a solvent system comprising a first solvent and a co-solvent to form a solution, wherein the co-solvent is an organic solvent having the dielectric constant less than about 10 at room temperature; and
(b) applying the solution onto the medical device to form the coating.

2. The method of claim 1, wherein the medical device is a stent.

3. The method of claim 1, wherein the co-solvent comprises unsubstituted or substituted aliphatic hydrocarbons, unsubstituted or substituted cycloaliphatic hydrocarbons, or unsubstituted or substituted aromatic hydrocarbons.

4. The method of claim 1, wherein the co-solvent is selected from a group consisting of n-pentane, n-hexane, n-heptane, cyclopentane, cyclohexane, benzene, toluene, tetrahydrofuran, carbon tetrachloride, methylene chloride, and mixtures thereof.

5. The method of claim 1, wherein a mass ratio between the first solvent and the co-solvent in the solvent system is within a range of between about 3:1 and 9:1.

6. The method of claim 1, wherein the first solvent is selected from a group consisting of dimethylacetamide and dimethylsulfoxide, and wherein the co-solvent is selected from a group consisting of n-pentane, n-hexane, n-heptane, cyclopentane, cyclohexane, benzene, toluene, tetrahydrofuran, carbon tetrachloride, methylene chloride, and mixtures thereof.

7. A method for coating an implantable medical device, comprising:
(a) dissolving a poly(ethylene-co-vinyl alcohol) and a drug in a solvent system comprising a first solvent and a co-solvent to form a solution, wherein the co-solvent is an organic solvent having surface energy less than about 30 dyne/cm at room temperature; and
(b) applying the solution onto the medical device to form the coating.

8. The method of claim 7, wherein the medical device is a stent.

9. The method of claim 7, wherein the co-solvent comprises substituted or unsubstituted aliphatic hydrocarbons, unsubstituted or substituted cycloaliphatic hydrocarbons, or unsubstituted or substituted aromatic hydrocarbons.

10. The method of claim 7, wherein the co-solvent is selected from a group consisting of n-pentane, n-hexane, n-heptane, cyclopentane, cyclohexane, benzene, toluene, tetrahydrofuran, carbon tetrachloride, methylene chloride, and mixtures thereof.

11. The method of claim 7, wherein a mass ratio between the first solvent and the co-solvent in the solvent system is within a range of between about 3:1 and 9:1.

12. The method of claim 7, wherein the first solvent is selected from a group consisting of dimethylacetamide and dimethylsulfoxide, and wherein the co-solvent is selected from a group consisting of n-pentane, n-hexane, n-heptane, cyclopentane, cyclohexane, benzene, toluene, tetrahydrofuran, carbon tetrachloride, methylene chloride, and mixtures thereof.

13. A method for coating an implantable medical device, comprising:
(a) dissolving a poly(ethylene-co-vinyl alcohol) and a drug in a solvent system comprising a first solvent and a co-solvent to form a solution, wherein the co-solvent is an organic solvent having a viscosity not exceeding about 1 centipoise at room temperature; and
(b) applying the solution onto the medical device to form the coating.

14. The method of claim 13, wherein the medical device is a stent.

15. The method of claim 13, wherein the co-solvent comprises unsubstituted or substituted aliphatic hydrocarbons, unsubstituted or substituted cycloaliphatic hydrocarbons, or unsubstituted or substituted aromatic hydrocarbons.

16. The method of claim 13, wherein the co-solvent is selected from a group consisting of n-pentane, n-hexane, n-heptane, cyclopentane, cyclohexane, benzene, toluene, tetrahydrofuran, carbon tetrachloride, methylene chloride, and mixtures thereof.

17. The method of claim 13, wherein a mass ratio between the first solvent and the co-solvent in the solvent system is within a range of between about 3:1 and 9:1.

18. The method of claim 13, wherein the first solvent is selected from a group consisting of dimethylacetamide and dimethylsulfoxide, and wherein the co-solvent is selected from a group consisting of n-pentane, n-hexane, n-heptane, cyclopentane, cyclohexane, benzene, toluene, tetrahydrofuran, carbon tetrachloride, methylene chloride, and mixtures thereof.

* * * * *